US011395886B2

(12) United States Patent
Umanskiy et al.

(10) Patent No.: US 11,395,886 B2
(45) Date of Patent: Jul. 26, 2022

(54) CAPACITIVE SINGLE PLATE BUBBLE DETECTOR

(71) Applicant: BAXTER CORPORATION ENGLEWOOD, Englewood, CO (US)

(72) Inventors: Yuriy Konstantinovich Umanskiy, Centennial, CO (US); David Lee Holien, Parker, CO (US); Brian William Ward, Littleton, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 55 days.

(21) Appl. No.: 17/111,024

(22) Filed: Dec. 3, 2020

(65) Prior Publication Data
US 2021/0085892 A1 Mar. 25, 2021

Related U.S. Application Data

(62) Division of application No. 16/066,983, filed as application No. PCT/US2016/068244 on Dec. 22, 2016, now Pat. No. 10,881,812.

(60) Provisional application No. 62/272,794, filed on Dec. 30, 2015.

(51) Int. Cl.
G01R 27/26 (2006.01)
A61M 5/36 (2006.01)
G01D 5/24 (2006.01)
A61M 5/168 (2006.01)
A61M 5/142 (2006.01)

(52) U.S. Cl.
CPC ............ *A61M 5/365* (2013.01); *A61M 5/142* (2013.01); *A61M 5/16831* (2013.01); *G01D 5/2405* (2013.01); *A61M 2205/3317* (2013.01); *A61M 2205/702* (2013.01)

(58) Field of Classification Search
USPC .................................. 324/663–665, 679, 689
See application file for complete search history.

(56) References Cited

U.S. PATENT DOCUMENTS

2014/0239982 A1  8/2014  Alameh et al.
2016/0207204 A1* 7/2016  Teuscher .................. G01D 5/24

FOREIGN PATENT DOCUMENTS

EP        2522554 A1    11/2012

OTHER PUBLICATIONS

International Search Report for related International Application No. PCT/US2016/068244; report dated Mar. 23, 2017; (3 pages).
Written Opinion for related International Application No. PCT/US2016/068244; report dated Mar. 23, 2017; (6 pages).

* cited by examiner

Primary Examiner — Vincent Q Nguyen
(74) Attorney, Agent, or Firm — K&L Gates LLP

(57) ABSTRACT

A single plate capacitive bubble detection sensor. The detector may employ a single active plate. A parasitic capacitance of the active plate relative to the environment may be monitored without reference to any particular ground source. In this regard, highly sensitive measurements may be made of a tube disposed adjacent to the active plate to detect, for example, the presence of air, liquid, or a change between liquid and air in the tube.

16 Claims, 8 Drawing Sheets

CAPACITIVE SINGLE PLATE BUBBLE DETECTOR

PRIORITY CLAIM AND CROSS-REFERENCE TO RELATED APPLICATIONS

The present application is a divisional of U.S. patent application Ser. No. 16/066,983 filed Jun. 28, 2018, entitled "CAPACITIVE SINGLE PLATE BUBBLE DETECTOR," which was a National Stage filing of International Application No. PCT/US2016/068244, filed on Dec. 22, 2016, which claims priority to U.S. Provisional Patent Application No. 62/272,794 filed Dec. 30, 2015, entitled "CAPACITIVE SINGLE PLATE BUBBLE DETECTOR," which is incorporated herein by reference in its entirety. This application relates to and incorporates by reference the co-owned U.S. Provisional Patent Application No. 62/272,786 filed on Dec. 30, 2015 entitled "SYRINGE POSITIONING APPARATUS AND METHOD". This application relates to and incorporates by reference the co-owned U.S. Provisional Patent Application No. 62/272,789 filed Dec. 30, 2015, entitled "MEASUREMENT OF SYRINGE GRADUATION MARKS USING A VISION SYSTEM." This application relates to and incorporates by reference the co-owned U.S. patent application Ser. No. 14/984,022 filed on Dec. 30, 2015 entitled "SOURCE FLUID INLET ASSEMBLY FOR AUTOMATED FILLING DEVICE". This application relates to and incorporates by reference the co-owned U.S. Provisional Patent Application No. 62/272,798 filed on Dec. 30, 2015 entitled "SYRINGE GRIPPING APPARATUS AND METHOD". This application relates to and incorporates by reference the co-owned U.S. patent application Ser. No. 14/984,285 filed on Dec. 30, 2015 entitled "SYRINGE PLUNGER POSITION APPARATUS AND METHOD". This application relates to and incorporates by reference the co-owned U.S. patent application Ser. No. 15/360,365 filed on Nov. 23, 2016 entitled "LABEL APPLICATOR FOR SYRINGE LABELING". This application relates to and incorporates by reference the co-owned U.S. Provisional Patent Application No. 62/272,816 filed on Dec. 30, 2015 entitled "INLET TUBE SET FOR SOURCE INGREDIENT DELIVERY". This application relates to and incorporates by reference the co-owned U.S. patent application Ser. No. 14/984,913 filed on Dec. 30, 2015 entitled "TIP CAP FOR AUTOMATIC SYRINGE FILLING APPARATUS". This application relates to and incorporates by reference the co-owned U.S. patent application Ser. No. 15/179,643 filed on Jun. 10, 2016 entitled "TAMPER EVIDENT SYRINGE TIP CAP".

BACKGROUND

In many medical contexts, fluids are transferred via tubing or other conduits. It is often desirable to detect changes between air and liquid in the tubing used to transfer fluid. For example, when providing an intravenous infusion to a patient, fluid may be delivered via an IV tubing set to the patient. In this regard, air bubble detection may be important to detect air in the IV tubing prior to infusion into the patient to avoid air embolisms, which may cause harm to the patient. In other contexts, as fluid is transferred (e.g., during the preparation of a medication or the like), it is important to detect air in tubing to ensure a proper volume of fluid is being transferred or to detect when a source of fluid has been depleted. Furthermore, detection of a change from air to liquid may be advantageous for priming operations or the like.

A number of types of air bubble detectors have been proposed. These may include ultrasonic, optical, or paired plate capacitive type bubble detectors. However, these bubble detectors all suffer from drawbacks. Specifically, such detectors often require the tubing to be monitored to be disposed between opposing detectors. In this regard, the placement of the tubing between the detectors may require the tubing to be disposed in a particular arrangement and/or may require the tubing to be manually inserted between the detectors. This may add complexity to bubble detection as the tubing may be required to be carefully placed between the detectors. Furthermore, such detectors are often costly. In turn, the use of such detectors may be costly and may add complexity to systems or devices utilizing such detectors.

SUMMARY

In view of the foregoing, the present disclosure is generally related to a single plate capacitive bubble detector that may be used to monitor a tube to detect a change in the state of a tube from a first condition to a second condition. For example, the change in condition may be a change in a material within the tube between air and liquid. That is, the single plate capacitive bubble detector may be operative to sense fluid in a tube, air in a tube, or an interface (i.e., a change) between fluid and air in a tube. Such a change between fluid and air may comprise a change from fluid to air or may comprise a change from air to fluid. The present disclosure presents a capacitive bubble detector that has a single active sensor plate without any particular corresponding ground source or sensor.

A single plate capacitive bubble detector as described herein may provide a number of advantages over previously proposed sensors. As the capacitive detector described herein uses a single active sensor plate without a corresponding specifically provided ground source, a sensor portion of the capacitive detector may be relatively small because an area associated with a single active plate alone may be presented adjacent to the tube to be monitored. As such, the tubing to be monitored may be positioned adjacent a single side of the sensor portion such that the tubing need not be placed between, or in any specific relation relative to, any pair of detectors. Also, because no particular ground electrode is provided, the sensor portion may be disposed along a relatively small area of the tubing and still achieve highly accurate monitoring. In this regard, the portion of sensor that must be adjacent to the tubing may be reduced as compared to other prior sensors, thus enabling more potential uses and/or locations of a single plate capacitive bubble detector. That is, in applications where space is limited, the capacitive detector described herein may be more useful as it does not require specific positioning of tubing between elements of a sensor and may occupy a relatively small area adjacent to the tubing to achieve accurate bubble detection. For example, a sensor as described herein may be used in connection with a device having a plurality of tubes to be monitored. The tubes may be moved into position relative to the sensor for monitoring of a given one of the plurality of tubes.

Furthermore, the sensors described herein may achieve a relatively high resolution, thus providing very sensitive measurements related to the tubing being monitored. That is, because the sensor may, as described above, be provided and operated without reference to any particular ground source, the sensor may rely on the concept of "parasitic capacitance." Parasitic capacitance generally describes the resulting capacitance in a conductor based on the capacitive effects on the conductor due to the general environment. Accordingly, the resolution of the single plate sensor described herein may allow for sensing changes in capacitance of less than about 15 fF. That is, the resolution of the sensor may be greater than 0.3 fF. In this regard, the use of this parasitic capacitance is a fundamental shift from prior sensors that utilize specifically designed capacitive cells defined by cooperating sensor pairs.

Specifically, in a traditional capacitive sensor, two specific sensor elements (e.g., electrodes) are provided for measurement of capacitance between the two electrodes. Tubing placed between, or in specific relation to, these electrodes affects the dielectric constant (or permittivity) of the capacitor dielectric formed between the two specific electrodes. In turn, providing an electrical potential between the two electrodes allows the measurement of the capacitance of the two plate electrode pair that results based on the dielectric constant of the tubing depending on the material contained in the tubing between the sensors. This capacitance is measured and compared to known capacitances of tubing containing air and tubing containing a fluid. Specifically, as a liquid may have a much larger dielectric constant than air or other gasses, when liquid is present in the tube, the resulting capacitance may also be greater. As such, the sensed capacitance between the two elements of the sensor may be attributed to the dielectric constant between the specifically provided elements of the sensor, and may thus be used to detect the air or liquid in the tubing.

Use of these specifically paired plate sensors results in disadvantages as described above. Namely, the tubing to be monitored must be placed with specificity in relation to the sensors (e.g., between or in specific relation to paired plates), which may be difficult to achieve in certain contexts.

In turn, the use of a single plate sensor utilizing the parasitic capacitance of the single plate sensor may address at least some of the drawbacks of the prior approaches discussed above. Specifically, given that a single plate electrode may be used with the sensor, the overall size may be reduced and placement of the detector may be simplified as two plates need not be provided or specifically arranged relative to the tubing to be monitored. In turn, a highly accurate detection of changes in a monitored tube may be provided by a single plate that operates by way of measurement of the parasitic capacitance of the single plate without regard to any particular specific ground source.

However, use of the parasitic capacitance of the sensor may result in detection of capacitive changes resulting from environmental factors other than the dielectric changes of a monitored tube. For instance, because the capacitance of the single sensor plate is monitored in relation to the environment generally without regard to any particular ground source, changes in the environment surrounding the sensor may also be detected. These environmental changes may include changes in temperature, humidity, biometric pressure, electrical changes of surrounding electronic componentry, movement of devices and/or objects near the sensor, etc. In short, given the parasitic capacitance of the single plate is monitored in relation to the environment rather than in relation to any particular ground source, any change in the environment may also detected at the sensor, thus potentially complicating the detection of changes within the tube.

Accordingly, these environmental changes may be monitored and considered such that changes in the environment other than a change in the monitored tube do not result in false readings for the sensor. Specifically, it may be appreciated that such environmental changes occur much more slowly (e.g., at a lower frequency or at a slower rate of change) than a change resulting in a change in material flowing through the monitored tube. That is, the resulting change in parasitic capacitance due to an air/liquid interface passing the sensor in the tube may occur much more rapidly than changes associated with the environment (e.g., changes in ambient weather conditions, movement of objects near the sensor, etc.). Accordingly, band pass filtering or other signal processing techniques may be applied to a signal generated by the sensor such that environmental changes may be disregarded.

Furthermore, given the sensor may be affected by changes in parasitic capacitance in the single plate detector other than those resulting from a change in material in the monitored tube, a baseline capacitance may be established in relation to a known condition (e.g., air in the tube or liquid in the tube). In turn, any change in parasitic capacitance of the single plate sensor from the baseline that exceeds a threshold defined in relation to the baseline may indicate a sensed change in the tube (e.g., a change in material flowing in the tube monitored). That is, if a known condition of air in the tube is used establish a parasitic capacitance baseline, a deviation of capacitance from this baseline that exceeds the threshold established in relation to the baseline may indicate a change from air to fluid in the tube. Similarly, a baseline capacitance established in relation to a fluid in the tube may be used to detect a change to air in the tube by way of a change in parasitic capacitance of the single plate sensor that exceeds the threshold established in relation to the baseline.

The baseline may be periodically or continuously modified in relation to the environment such that changes due to an interface event in the tube may be detected. For example, some changes that are detected may be used to update the baseline value. In turn, environmental contributions to the parasitic capacitance other than the state of the monitored tube may be disregarded when monitoring the tube using the single plate sensor. For instance, relatively slow changes in the parasitic capacitance may be used to update the baseline.

Accordingly, a first aspect includes a capacitive sensor for detection of a change in a material flowing in a tube for communicating a liquid. The sensor includes a sensor body having a sensor portion with a reference surface on a first side of the sensor body. The reference surface is adapted for adjacent positioning of a tube relative to the reference surface such that a tube is disposed adjacent to only the first side of the sensor body along the reference surface. The sensor also includes an active plate comprising a conductive material that is disposed at and extends relative to the reference surface of the sensor portion. The sensor portion of the sensor body is devoid of any ground sources in an area coextensive with the extent of the active plate. In turn, the sensor includes a measurement module, executed by a processor, in operative communication with the active plate to measure a parasitic capacitance of the active plate in relation to an environment surrounding the active plate without reference to any particular ground source. As such, a change in a material flowing in a tube disposed adjacent to the sensor portion results in the parasitic capacitance of the active sensor relative to the environment to change such that the change in parasitic capacitance is detectable by the measurement module.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in an embodiment the sensor body may be a printed circuit board and the active plate may include a conductive trace of the printed circuit board. As such, a ground plane of the printed circuit board may not overlap any portion of the active plate. Specifically, the sensor portion may be devoid of any ground sources in an entirety of the sensor portion along which a tube extends when positioned adjacent to the sensor portion.

Additionally, the sensor may include a module to assist in accounting for changes in the parasitic capacitance of the active plate that are not related to a change in a material in a tube. In this regard, the sensor may include a calibration module, executed by a processor, operative to establish a baseline parasitic capacitance of the active sensor relative to the environment in the presence of a tube disposed adjacent to the active sensor in a first state. The measurement module may be operative to detect a change in a material flowing in a tube disposed adjacent to the sensor portion based on a change in the parasitic capacitance of the active sensor relative to the baseline parasitic capacitance established by the calibration module. For example, the baseline parasitic capacitance may be established in relation to a tube containing air. Accordingly, a change in the parasitic capacitance of the active sensor that exceeds a threshold capacitance value relative to the baseline may be indicative of a change to the tube containing a liquid. Additionally or alternatively, the baseline parasitic capacitance may be established in relation to a tube containing liquid. As such, a change in the parasitic capacitance of the active sensor greater than a threshold capacitive value relative to the baseline may be indicative of a change to the tube containing air. In an embodiment, the calibration module may be operative to periodically or continually update the baseline parasitic capacitance in response to changes in the parasitic capacitance of the active sensor. For instance, these changes may occur more slowly than a change in material in the tube. As such, a low pass filter may be utilized such that these slowly occurring changes are utilized to update the baseline.

In an embodiment of the sensor, the resolution (i.e., discrimination capability) of the capacitive sensor may be about 15 fF. Such a fine resolution may be in part due to the relatively small magnitude parasitic capacitance monitored by the sensor. For example, the parasitic capacitance of the active plate with a tube filled with a liquid disposed adjacent to the sensor portion may be less than about 10 pF. In other applications, the parasitic capacitance of the active plate with a tube filled with a liquid disposed adjacent to the sensor portion may be less than about 5 pF. For example, the parasitic capacitance of the active plate to the common ground may be between about 2 pF and 4 pF. In turn, the change in the parasitic capacitance of the active sensor in the presence of an air bubble in a tube disposed relative to the sensor portion relative to the parasitic capacitance of the active sensor in the presence of a liquid in a tube disposed relative to the sensor portion may result in a change in the parasitic capacitance of 0.1 to 0.2 pF. Furthermore, monitoring of the parasitic capacitance may allow for relatively high frequency monitoring of the parasitic capacitance of the active sensor. For instance, a scanning frequency corresponding to a rate at which the measurement module samples the parasitic capacitance of the active plate is greater than about 200 Hz.

A second aspect includes a method for detection of a change between liquid and air in a tube for communicating liquid. The second aspect includes establishing a baseline parasitic capacitance value of an active plate of a sensor corresponding to a first known state of an environment surrounding the active plate without reference to any particular ground source. The first known state of the environment comprises one of a liquid filled tube disposed adjacent to the active plate or an air filled tube disposed adjacent to the active plate. The method further includes monitoring a parasitic capacitance value of the active plate relative to the baseline parasitic capacitance value. The parasitic capacitance value is measured without reference to any particular ground source. Rather, the parasitic capacitance is measured in relation to a common ground of a totality of the environment in which the sensor is disposed (e.g., that includes the conductive parts of a device in which the sensor is disposed). The method further includes determining the parasitic capacitance value of the active plate exceeds a threshold value relative to the baseline parasitic capacitance value and indicating a change in state of the sensor to a second state corresponding to a different state than the first known state. The change in state corresponds to detection of an interface between liquid and air in a tube adjacent to the active plate.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For instance, the threshold value may correspond to a given capacitance value in relation to the baseline. Accordingly, the method may include updating the baseline parasitic capacitance value of the active plate based on a change in the parasitic capacitance value of the active plate that is not due to a change in material in the monitored tube. For instance, such changes may occur more slowly than changes in material in the tube. In this regard, the method may include generating an adaptive baseline that accounts for changes in the parasitic capacitance of the sensor due to changes in the environment surrounding the active plate other than changes in the tube to be monitored.

A third aspect includes a device for detection of a change in a material flowing in a tube for communicating a liquid. The device includes a capacitive sensor. The sensor includes a sensor body having a sensor portion with a reference surface on a first side of the sensor body. The sensor also includes an active plate comprising a conductive material that is disposed at and extends relative to the reference surface of the sensor portion. The sensor portion of the sensor body is devoid of any ground sources in an area coextensive with the extent of the active plate. The sensor also includes a measurement module, executed by a processor, in operative communication with the active plate to measure a parasitic capacitance of the active plate in relation to an environment surrounding the active plate without reference to any particular ground source.

The device may also include a tubing block for engagement of a plurality of tubes. The tubing block is moveable relative to the sensor body to dispose a corresponding one of the plurality of tubes relative to the reference surface. In this regard, the corresponding one of the plurality of tubes is disposed adjacent to only the first side of the sensor body along the reference surface, and a change in a material flowing in the corresponding one of the plurality of tubes disposed adjacent to the sensor portion results in the parasitic capacitance of the active sensor relative to the environment to change such that the change in parasitic capacitance is detectable by the measurement module.

A number of feature refinements and additional features are applicable to the third aspect. These feature refinements and additional features may be used individually or in any combination. As such, each of the following features that will be discussed may be, but are not required to be, used with any other feature or combination of features of the third aspect.

For example, each of the plurality of tubes is engageable with a different corresponding fluid source. The one of the plurality of tubes disposed relative to the reference surface may correspond to a fluid source engaged in a fluid transfer operation. As such, the device may be used in, or part of, a device that employs a plurality of fluid sources. As each fluid source is to be used in a fluid transfer operation, a corresponding one of the tubes may be moved into a position relative to the active sensor such that the active sensor may monitor the tube corresponding to the fluid source utilized. As the sensor may provide a relatively compact sensor portion that does not require specific or complicated placement of the tube relative to the sensor, the tubing block may provide for simple and reliable movement of a corresponding tube into position for accurate and precise monitoring of the tube.

Various embodiments may comprise any number of combinations of apparatus and/or method features described above and/or hereinbelow. Such combinations may include those encompassed by the following Embodiments:

1. A capacitive sensor for detection of a change in a material flowing in a tube for communicating a liquid, comprising:
    a sensor body comprising a sensor portion having a reference surface on a first side of the sensor body that is adapted for adjacent positioning of a tube relative to the reference surface such that a tube is disposed adjacent to only the first side of the sensor body along the reference surface;
    an active plate comprising a conductive material that is disposed at and extends relative to the reference surface of the sensor portion, wherein the sensor portion of the sensor body is devoid of any ground sources in an area coextensive with the extent of the active plate;
    a measurement module, executed by a processor, in operative communication with the active plate to measure a parasitic capacitance of the active plate in relation to an environment surrounding the active plate without reference to any particular ground source, wherein a change in a material flowing in a tube disposed adjacent to the sensor portion results in the parasitic capacitance of the active sensor relative to the environment to change such that the change in parasitic capacitance is detectable by the measurement module.

2. The capacitive sensor of Embodiment 1, wherein the sensor body comprises a printed circuit board and the active plate comprise a conductive trace of the printed circuit board.

3. The capacitive sensor of Embodiment 1 or 2, wherein a ground plane of the printed circuit board does not overlap any portion of the active plate.

4. The capacitive sensor of any one of the Embodiments 1-3, wherein the sensor portion is devoid of any ground sources in an entirety of the sensor portion along which a tube extends when positioned adjacent to the sensor portion.

5. The capacitive sensor of any one of the Embodiments 1-4, further comprising:
    a calibration module, executed by a processor, operative to establish a baseline parasitic capacitance of the active sensor relative to the environment in the presence of a tube disposed adjacent to the active sensor in a first state.

6. The capacitive sensor of any one of the Embodiments 1-5, wherein the measurement module is operative to detect a change in a material flowing in a tube disposed adjacent to the sensor portion based on a change in the parasitic capacitance of the active sensor relative to the baseline parasitic capacitance established by the calibration module.

7. The capacitive sensor of any one of the Embodiments 1-6, wherein the baseline parasitic capacitance is established in relation to a tube containing air, and wherein a change in the parasitic capacitance of the active sensor greater than a threshold is indicative of a change to the tube containing a liquid.

8. The capacitive sensor of any one of the Embodiments 1-7, wherein the baseline parasitic capacitance is established in relation to a tube containing liquid, and wherein a change in the parasitic capacitance of the active sensor greater than a threshold is indicative of a change to the tube containing air.

9. The capacitive sensor of any one of the Embodiments 1-8, wherein the calibration module is operative to periodically update the baseline parasitic capacitance in response to changes in the parasitic capacitance of the active sensor resulting from environmental changes other than a change in material in the tube.

10. A method for detection of a change between liquid and air in a tube for communicating liquid, comprising:
    establishing a baseline parasitic capacitance value of an active plate of a sensor corresponding to a first known state of an environment surrounding the active plate without reference to any particular ground source, wherein the first known state of the environment comprises one of a liquid filled tube disposed adjacent to the active plate or an air filled tube disposed adjacent to the active plate;
    monitoring a parasitic capacitance value of the active plate relative to the baseline parasitic capacitance value, wherein the parasitic capacitance value is measured without reference to any particular ground source;
    determining the parasitic capacitance value of the active plate exceeds a threshold relative to the baseline parasitic capacitance value; and
    indicating a change in state of the sensor to a second state corresponding to a different state than the first known state, wherein the change in state corresponds to detection of an interface between liquid and air in a tube adjacent to the active plate.

11. The method of Embodiment 10, wherein the threshold comprises a predetermined change in magnitude of the parasitic capacitance value.

12. The method of Embodiments 10 or 11, further comprising:
    updating the baseline parasitic capacitance value of the active plate based on a relatively slow change in the parasitic capacitance value of the active plate.

13. A device for detection for detection of a change in a material flowing in a tube for communicating a liquid, comprising:
    a capacitive sensor comprising:
        a sensor body comprising a sensor portion having a reference surface on a first side of the sensor body,
        an active plate comprising a conductive material that is disposed at and extends relative to the reference surface of the sensor portion, wherein the sensor portion of the sensor body is devoid of any ground sources in an area coextensive with the extent of the active plate, and a measurement module, executed by a processor, in operative communication with the active plate to measure a parasitic capacitance of the active plate in relation to an environment surrounding the active plate without reference to any particular ground source; and a tubing block for engagement of a plurality of tubes, wherein the tubing block is moveable relative to the sensor body to dispose a corresponding one of the plurality of tubes relative to the reference surface such that the corresponding one of the plurality of tubes is disposed adjacent to only the first side of the sensor body along the reference surface, and wherein a change in a material flowing in the corresponding one of the plurality of tubes disposed adjacent to the sensor portion results in the parasitic capacitance of the active sensor relative to the environment to change such that the change in parasitic capacitance is detectable by the measurement module.

14. The device of Embodiment 15, wherein each of the plurality of tubes is engageable with a corresponding different fluid source.

15. The device of Embodiment 14 or 15, wherein the corresponding one of the plurality of tubes disposed relative to the reference surface corresponds to a fluid source engaged in a fluid transfer operation.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
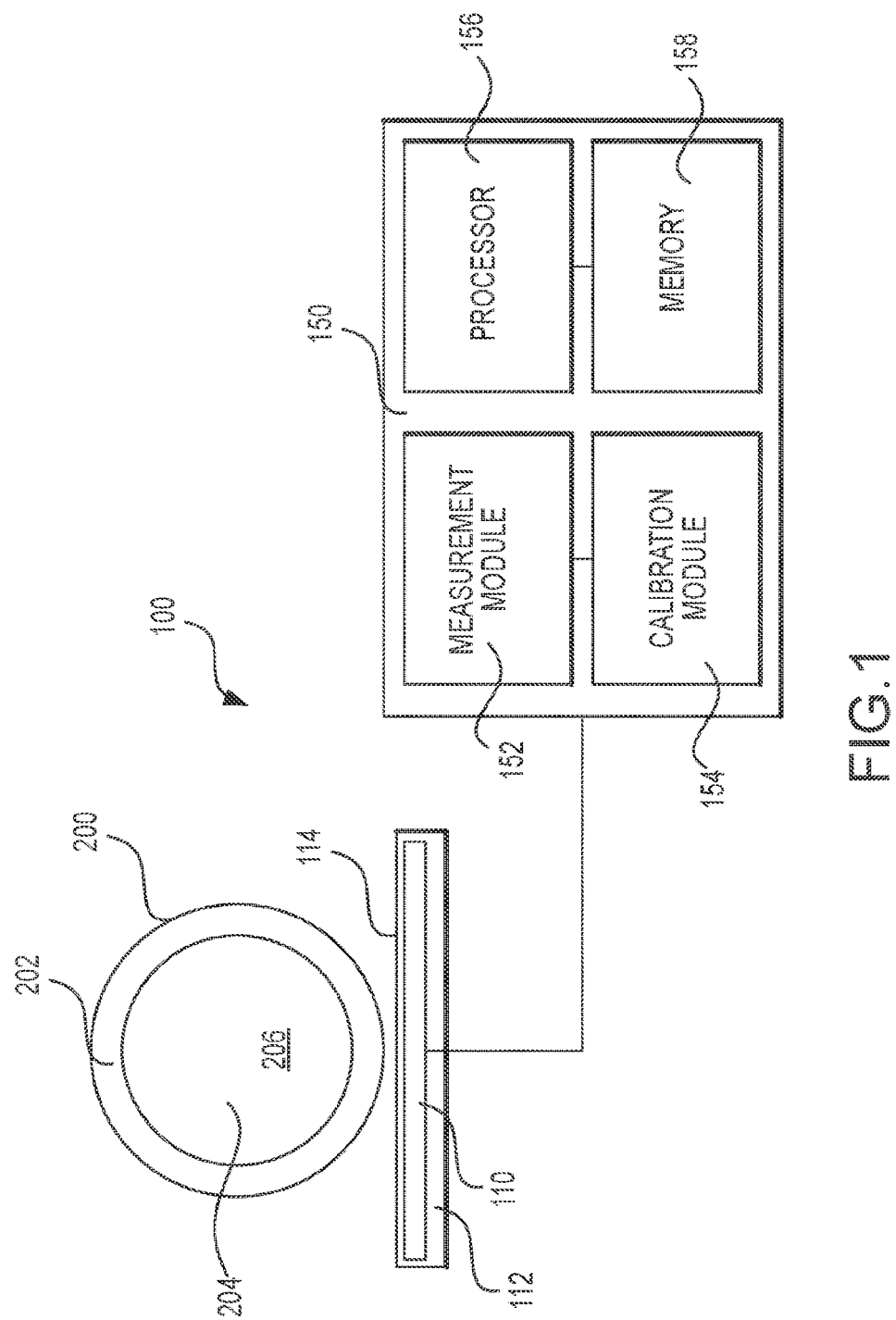
FIG. 1 depicts a schematic view of an embodiment of a single plate captive sensor disposed in relation to a tube containing air.

With reference to FIG. 1, an embodiment of a single plate sensor 100 is depicted schematically. The sensor 100 may include a sensor portion 112 and a processing module 150.

The sensor portion 112 and processing module 150 may be integral or may be provided separately. In either regard, the sensor portion 112 is in operative communication with the processing module 150. Specifically, the processing module 150 may be in operative electrical communication with an active plate 110 of the sensor portion 112. The active plate 110 may be provided in relation to a reference surface 114 of the sensor portion 112. The active plate 110 may be a conductive material that extends relative to the reference surface 114 of the sensor portion 112.

Figure 2:
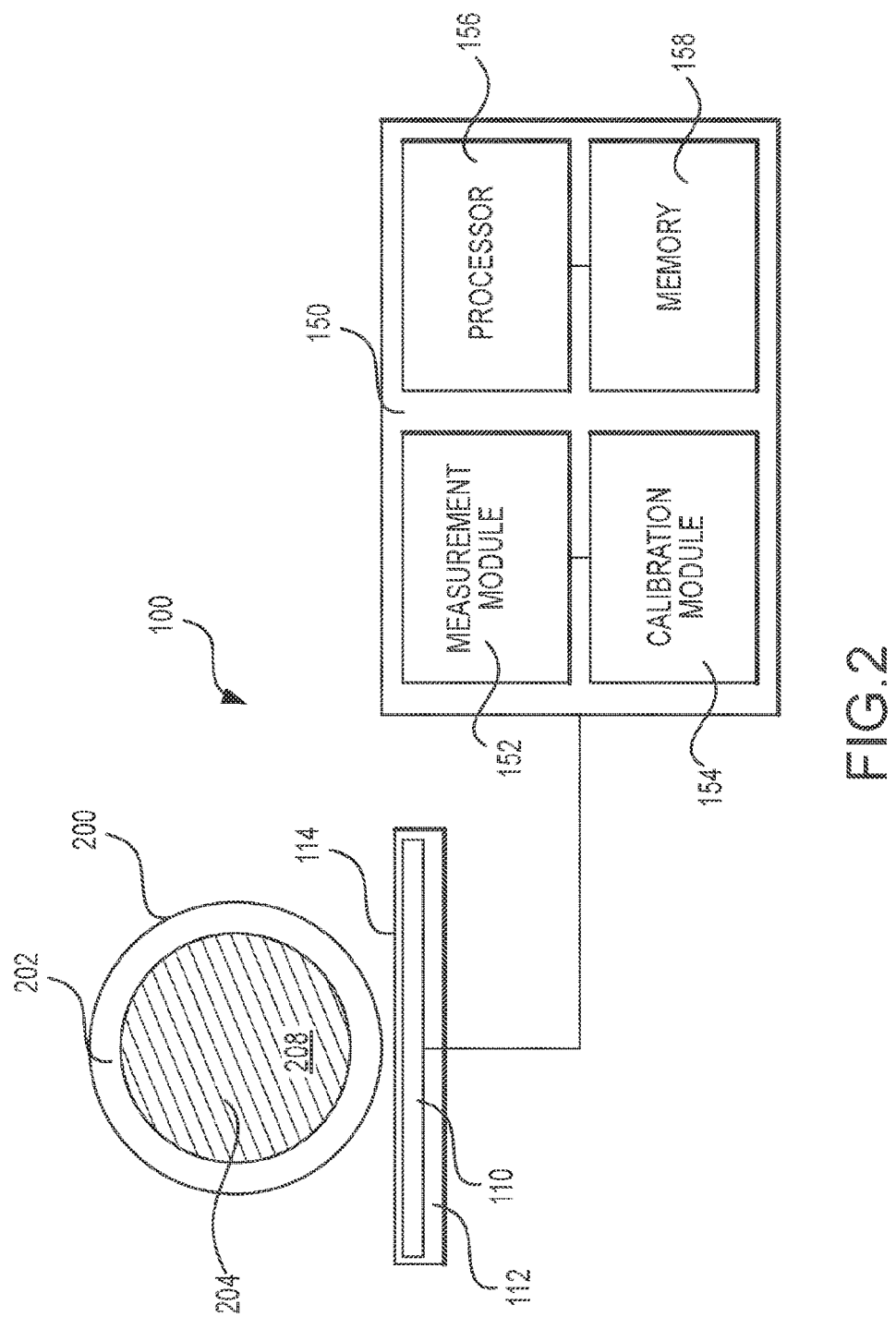
FIG. 2 depicts a schematic view of an embodiment of a single plate captive sensor disposed in relation to a tube containing liquid.

In turn, a tube 200 may be disposed relative to the reference surface 114 of the sensor portion 112. Note that while the tube 200 may be provided in contact with the sensor portion 112, the tube 200 need not be in direct contact with the sensor portion 112. For example, the tube 200 may be spaced up to about 2 mm from the sensor portion 112 and still achieve accurate monitoring of the tube 200. The tube 200 may include a nonconductive sidewall 202 that defines a lumen 204. The lumen 204 may comprise a fluid passageway through which a liquid 208 (as shown in FIG. 2) may flow in connection with a fluid transfer operation. In turn, the lumen 204 may also contain air 206. Accordingly, the tube 200 may be used in conjunction with any number of devices and/or operations. For instance, the tube 200 may be an intravenous injection tube used to introduce liquid intravenously to a patient. Additionally or alternatively, the tube 200 may be associated with a medical device such as, for example, a syringe filler, an infusion pump, a compounder, or other device that incorporates fluid transfer via tubing such as the tube 200. While the sensor 100 may be particularly suited for contexts in the field of medical devices and medical care, the sensor 100 may have other uses outside of the context of medical devices and medical care where the material in a tube 200 is to be monitored to detect changes between liquid 208 and air 206.

The processing module 150 may include a processor 156 (e.g., a physical computer processor device) in operative communication with a memory 158. In this regard, the processor 156 may be operative to access machine readable instructions comprising non-transitory machine readable data in the memory 158. The machine readable data stored in the memory 158 may be operative to specifically configure the processor 156 for performance of various functions described herein. As such, the processor 156 may be transformed from a general purpose computing processor to a specifically configured processor for accomplishing functionality related to various modules described herein upon access and execution of the data stored in the memory 158. For instance, various functionality is described herein as being executed by a processor of a module. Such modules may correspond to the processing module 150 generally or may relate to specific modules to be discussed in greater detail below. As may be appreciated, each module described herein may be an individual, discrete module having a corresponding processor 156 and memory 158 as described above where the memory 158 stores non-transitory machine readable data to configure the processor 156 to function as described in relation to a given module. Alternatively, multiple modules may be performed by a single processor 156 in communication with one or more physical memory devices comprising the memory 158. In this regard, the modules may correspond to different portions of non-transitory machine readable data stored in one or more physical memory devices. Further still, various ones or all of the modules may be executed using specifically configured hardware and/or software such as field programmable gate arrays, application specific integrated circuits, or the like. As such, the functionality of the various modules may be described herein in relation to functionality with the understanding that the functionality may be accomplished using any of the hardware, software, data, or techniques described herein.

The processing module 150 may include a measurement module 152 that may be operative to measure the parasitic capacitance of the active plate 110 without reference to any particular ground source but the common ground of the totality of the environment in which the sensor 100 is disposed. In turn, the measurement module 152 may be operable to measure an absolute parasitic capacitance value for the active plate 110 and/or monitor for changes in the parasitic capacitance of the active plate 110. That is, the measurement module 152 may output a value corresponding to the parasitic capacitance value for the active plate 110 (e.g., for further processing by the processing module 150). Additionally or alternatively, the measurement module 152 may output an indication of a change in parasitic capacitance corresponding to a change in material in a monitored tube. The indication may include information regarding the change (e.g., specific indication of a change from air to liquid or from liquid to air). Accordingly, the measured parasitic capacitance may be monitored and/or output for use in monitoring the tube 200 as will be described in greater detail below.

As addressed above, the active plate 110 may experience parasitic capacitance with respect to an environment surrounding the active plate 110 without reference to a specific ground source. In turn, the measurement module 152 may be operative to measure the parasitic capacitance of the active plate 110 with respect to the environment without specific reference to any particular ground source. By measuring the parasitic capacitance of the active plate 110 without respect to any particular ground source, no specific ground source need be provided in any particular arrangement relative to the active plate 110 or tube 200. That is, with respect to FIGS. 1 and 2, the active plate 110 may be the only electrode in communication with the measurement module 152 for measuring capacitance relative to the tube 200. In turn, no ground electrode or any other active electrode is provided in relation to the tube 200 for measurement of capacitance. As addressed above, this provides a number of benefits including improved characteristics of the sensor 100 for placement relative to the tube 200. That is, because a single active plate 110 is provided, only the active plate 110 need be positioned adjacent to the tube 200 for monitoring the tube 200. The tube 200 need not be disposed between or relative to a pair of sensors elements.

The parasitic capacitance of the active plate 110 may be affected by environmental factors other than a change of material (e.g., between fluid 208 and air 206) in the lumen 204 of the tube 200. Specifically, because the parasitic capacitance of the active plate 110 may be caused at least in part based on the dielectric constant of the totality of the environment surrounding the active plate 110, any changes in the environment surrounding the active plate 110 may affect the parasitic capacitance of the active plate 110. For instance, environmental changes such as changes in humidity, temperature, barometric pressure, or the like results in a change in parasitic capacitance of the active plate 110. Furthermore, other changes in the environment such as positioning of devices adjacent to the sensor 100, changes in electromagnetic fields and the environment in which the sensor 100 is disposed (e.g., due to adjacent electronics or ambient electromagnetic fields such as radiofrequency broadcasts or the like), or other variables in the environment may affect the parasitic capacitance of the active plate 110. However, these changes in the environment other than the change of the material in the lumen 204 of the tube 200 may occur relatively slowly (i.e., at a lower frequency) compared to the change in capacitance resulting from a change of the material in the lumen 204 of the tube 200.

Accordingly, a calibration module 154 may be provided at the processing module 150 to assist in signal processing of a signal of the measurement module 152 representative of the parasitic capacitance of the active plate 110 to account for such relatively slow (i.e., low frequency) changes in the parasitic capacitance that result from environmental changes other than the change of the material in the lumen 204 of the tube 200. That is, the environmental factors capable of changing the parasitic capacitance of the active plate 110 may occur more slowly than the resulting change in parasitic capacitance of the active plate 110 when a material change occurs within the lumen 204 of the tube 200. In turn, signal processing may be applied to the measured parasitic capacitance value of the active plate 110 to disregard changes due only to environmental factors other than a change in the lumen 204 of the tube 200.

One such example of signal processing that may be applied includes band pass filtering. For instance, a high pass filter may be provided by the calibration module 154 that may pass only relatively high frequency changes in a signal representing the parasitic capacitance of the active plate 110. In turn, after applying the high pass filter to the signal, only high frequency changes such as those associated with the change capacitance due to an abrupt change of material within lumen 204 of the tube 200 may be considered by the processing module 150 when monitoring the tube 200.

Still further, the calibration module 154 may be operative to generate an adaptive baseline that may be established for detecting a change of the monitored capacitance relative to the baseline using threshold detection. That is, a baseline value for the parasitic capacitance of the active plate 110 may be established in relation to a condition associated with the tube 200 (e.g., the presence of liquid 208 or the presence of air 206). The condition for which the baseline is established may be a known condition associated with a known material disposed in the tube 200 at the time of creation of the baseline. This baseline value may be utilized such that only changes in parasitic capacitance of the active plate 110 greater than a threshold value relative to the baseline value may result in detection of a change in the state of the tube 200 in relation to the presence of liquid 208 or air 206 in the lumen 204 of the tube 200.

Furthermore, to accommodate for changing environmental conditions, this baseline value may be adaptive. That is, changes (e.g., such as those resulting from changes in the environment other than a change in the material in the lumen 204 of the tube 200) may be utilized to update the baseline value corresponding to the ambient environment in which the active plate 110 is disposed. Accordingly, these low frequency factors that affect the parasitic capacitance may be utilized to update the adaptive baseline value. In turn, the adaptive baseline value may be updated (e.g., periodically or constantly) for use in detection of a change in the condition of the tube 200 associated with a variance from the baseline value that exceeds the threshold.

Accordingly, the measurement module 152 may be operative to monitor the parasitic capacitance of the active plate 110 to detect a change in the material in the lumen 204 of the tube 200. Specifically, as addressed above, the change in the parasitic capacitance may be indicative of a change from air 206 to liquid 208 or from liquid 208 to air 206 in the tube 200. As such, in either instance, the adaptive baseline value may be established for a first condition of the tube 200. In turn, a detected change in capacitance from the baseline value greater than a threshold value may result in the measurement module 152 indicating to the processing module 150 a change in the tube 200. As the baseline may be set with air 206 present, the change may correspond to detection of liquid within the tube 200. For instance, this may be utilized when priming the tubing 200 to detect when fluid has entered the tubing 200.

Correspondingly, a baseline value may be established with liquid 208 within the tube 200 such that a detected change in the state of the tube 200 based on a change in parasitic capacitance of the active plate 110 may result in the measurement module 152 indicating air in the tube 200. This may be indicative of an air bubble in the tube 200 or may be indicative that a source of the fluid flowing through the tube 200 is empty and requires changing. Either way, the variance from the baseline value established with liquid 208 in the tube 200 greater than a threshold value may result in detection of air within the tube 200 such that further alerting or action by the processing module 150 may occur. As the baseline value established for either condition may be periodically or continually updated to reflect changes to the environment surrounding the active plate 110 other than the change of the material within the lumen 204 of the tube 200, such changes in the environment may be accounted for by the updated adapted baseline value in determining a change in the material in the tube 200.

Accordingly, the processing module 150 may receive and/or process an indication of a change in the parasitic capacitance of the active sensor 110 based on the measured parasitic capacitance of the active sensor 110. In turn, the processing module 150 may be operative to generate an alert corresponding to the detected change. For example, the processing module 150 may output a human perceivable alert. Furthermore, the processing module 150 may be in operative communication with a device (e.g., a syringe filler, compounder, pump, etc.) to cease operation of the device upon detection of a change in the material in the tube 200. As addressed above, upon detection of a change in a material in a tube 200, an action may be taken such as, for example, termination of a priming operation, changing of a fluid source, verification and/or clearing of an air bubble in the tube, or other appropriate action. In this regard, the generation of an alert and/or signal to cease an operation may allow for such action to be taken.

Figure 3:
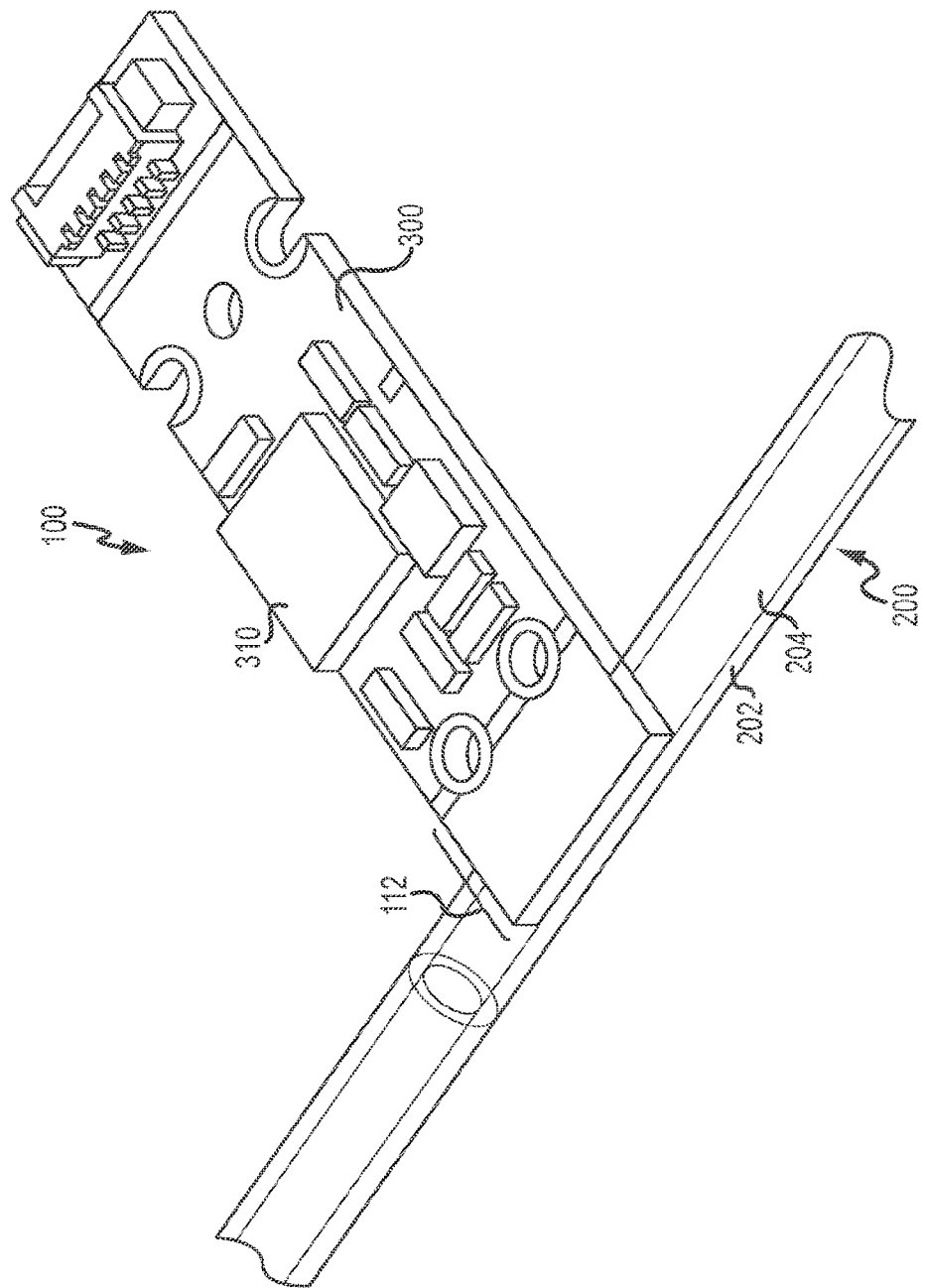
FIGS. 3 and 4 depicts perspective views of an embodiment of single plate capacitive sensor comprising a printed circuit board.
Figure 4:
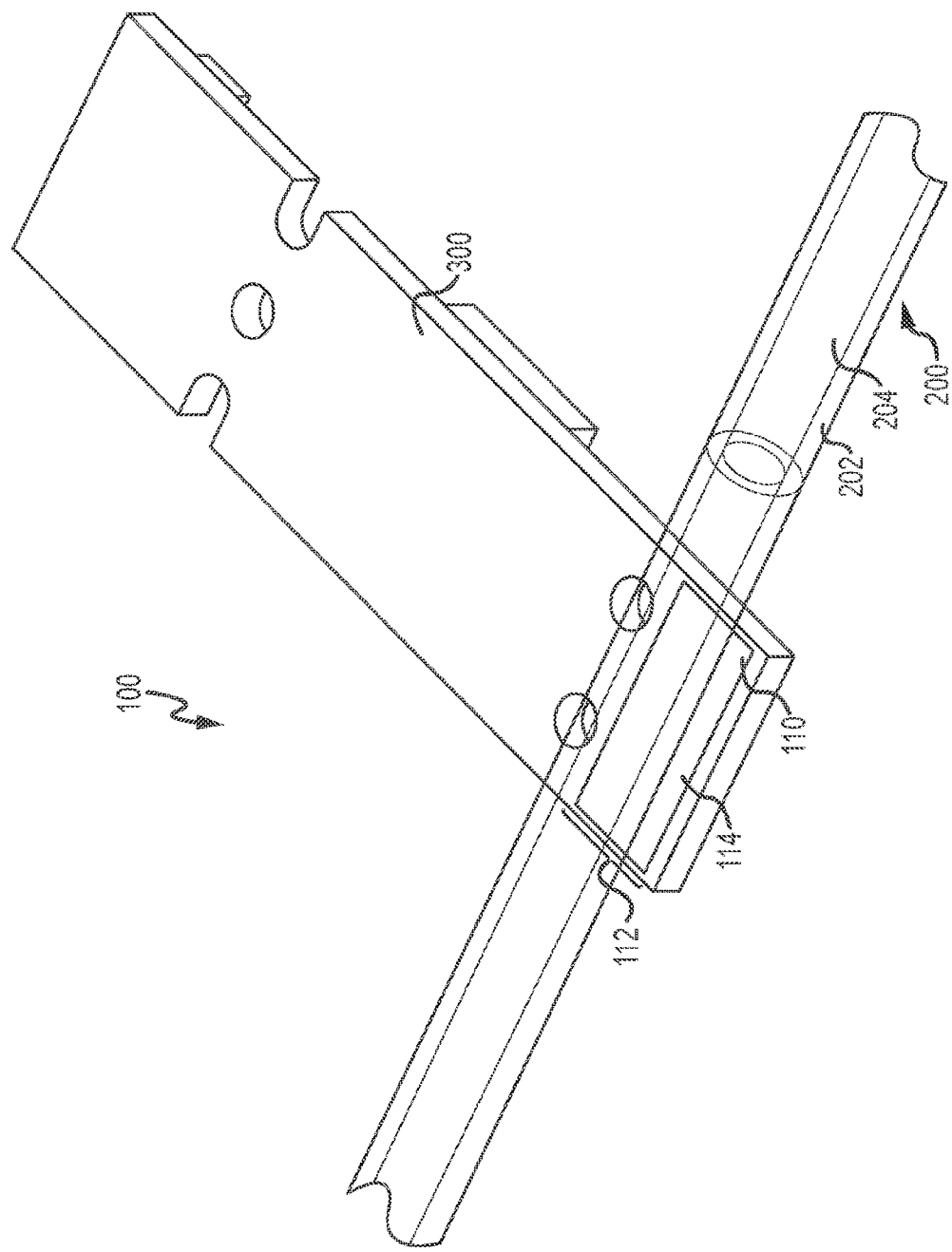

With further reference to FIGS. 3 and 4, an embodiment of a sensor 100 is depicted. In this regard, the sensor 100 may comprise a printed circuit board 300. The printed circuit board 300 may include hardware components 310 capable of executing the processing module 150 including the measurement module 152 and calibration module 154 as addressed above. In this regard, the printed circuit board 300 may include traces, vias, passive electronic components necessary for functionality of the hardware, or other common structures to establish electrical communication between corresponding ones of the appropriate hardware portions 310. The printed circuit board 300 may also include a sensor portion 112 having a reference surface 114 (best seen in FIG. 4). A tube 200 may be disposed adjacent to the reference surface 114 on a single given side of the printed circuit board 300. In this regard, the active plate 110 may comprise a conductive trace in a region of the printed circuit board 300. That is, the active plate 110 may be comprised of a conductive strip in one or more of the PCB conductive layers.

As may be appreciated, printed circuit boards such as the printed circuit board 300 of the embodiment depicted in FIGS. 3 and 4 often include ground planes for use in establishing electrical circuits among the components 310 provided on the printed circuit board 300. However, as described above, the active plate 110 may be provided in the absence of any ground source in the area of the active plate 110 in the sensor portion 112 (e.g., the sensor portion 112 which extends relative to the tube 200 may be devoid of any ground sources in the area coextensive with the tube 200 to be monitored).

Figure 5:
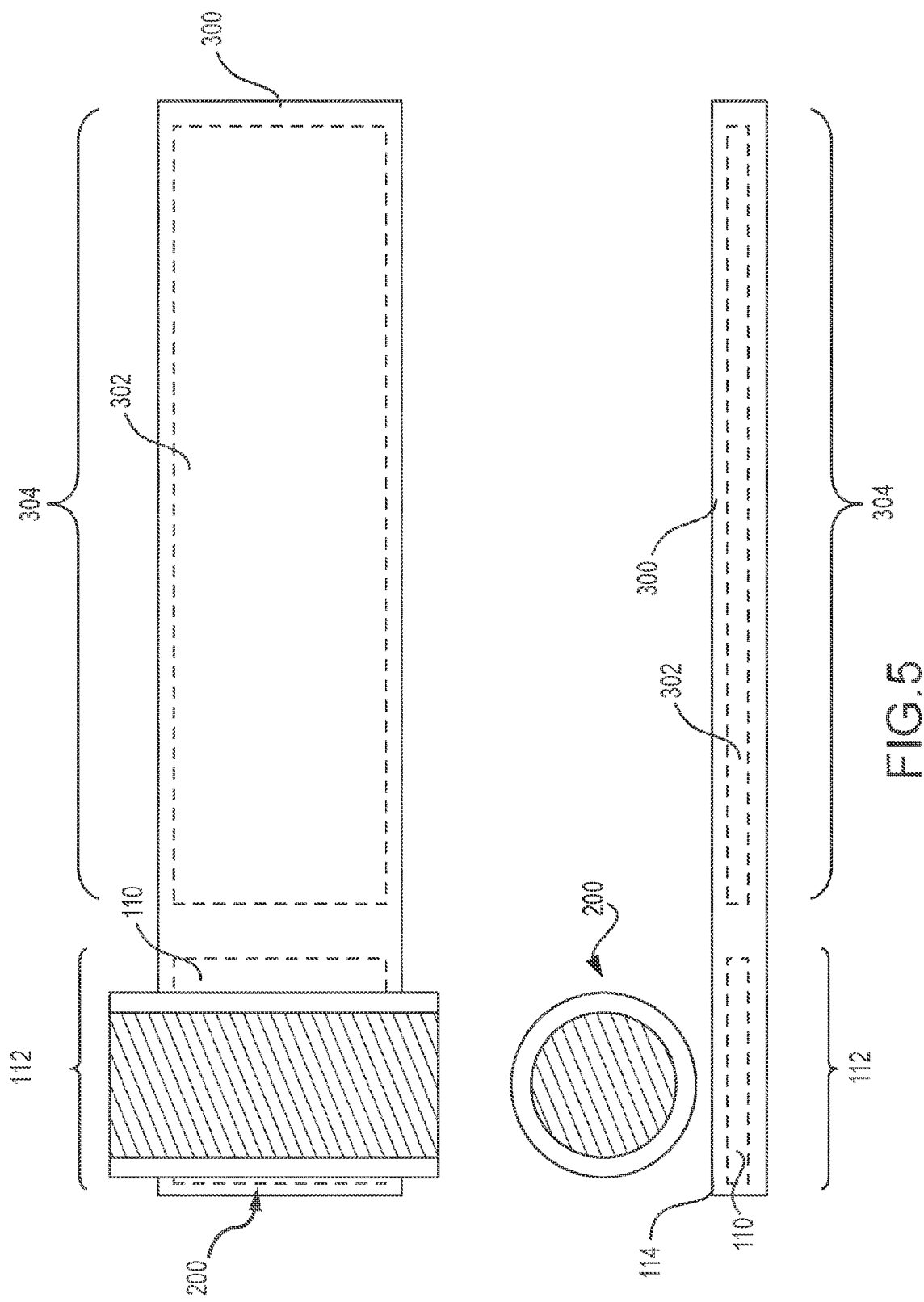
FIG. 5 depicts a top and side view of a printed circuit board showing an active plate in relation to a ground plane of the printed circuit board.

Accordingly, with further reference to FIG. 5, a top and side view of the printed circuit board 300 is depicted. The active plate 110 is depicted as a printed trace of conductive material in the area of the sensor portion 112. Additionally, a ground plane 302 is depicted. As may be appreciated, the ground plane 302 may be, but does not have to be, provided in a portion of the sensor body 304 that is mutually exclusive from the sensor portion 112. That is, the ground plane 302 of the printed circuit board 300, if present, may not extend relative to the active plate 110 at any portion of the active plate 110. That is, the ground plane 302 of the printed circuit board 300 may not overlap any portion of the active plate 110. As such, when the tube 200 is disposed adjacent to the reference surface 114 in the area of the sensor portion 112, the ground plane 302 may not extend relative to the tube 200 such that the ground plane 302 does not act as a specific ground source relative to the tube 200. While the ground plane 302 may exist in the environment surrounding the active plate 110, and thereby may contributes to the parasitic capacitance of the active plate 110, the capacitance between the active plate 110 and the ground plane 302 is not specifically measured and any contribution of the parasitic capacitance of the active plate 110 due to the ground plane 302 is not specifically determined. Accordingly, the ground plane 302 may form a portion of the environment relative to which parasitic capacitance of the active plate 110 is measured, however, no specific measure of the capacitance between the active plate 110 in the ground plane 302 is monitored. Accordingly, any contribution to the parasitic capacitance by the ground plane 302 contributes to the environmental factors to parasitic capacitance that is accommodated for in the analysis of the parasitic capacitance signal for the active plate 110 by way of contributing to the baseline value that is adaptively established.

Figure 6:
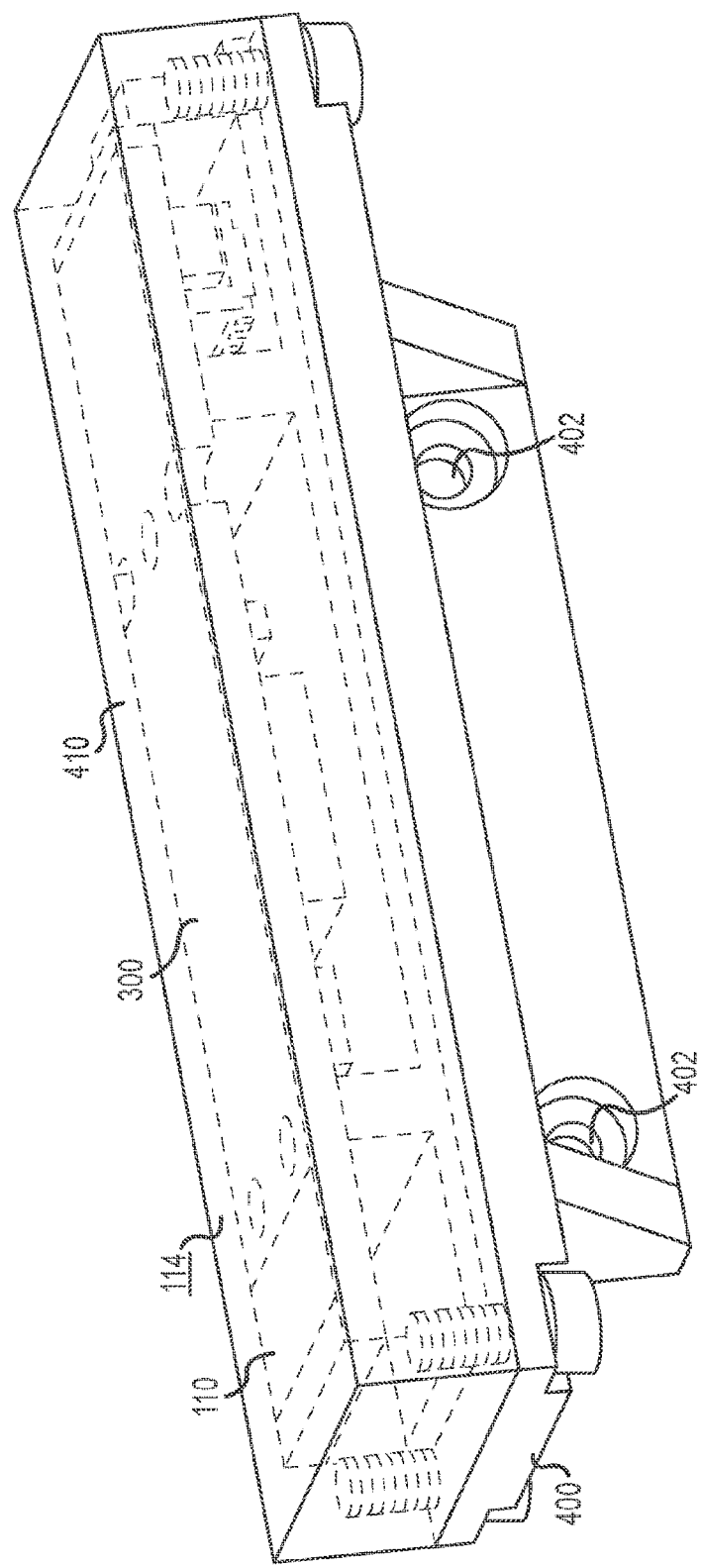
FIG. 6 depicts a perspective view of an embodiment of a sensor disposed in a mounting chassis for mounting relative to or with a device.
Figure 7:
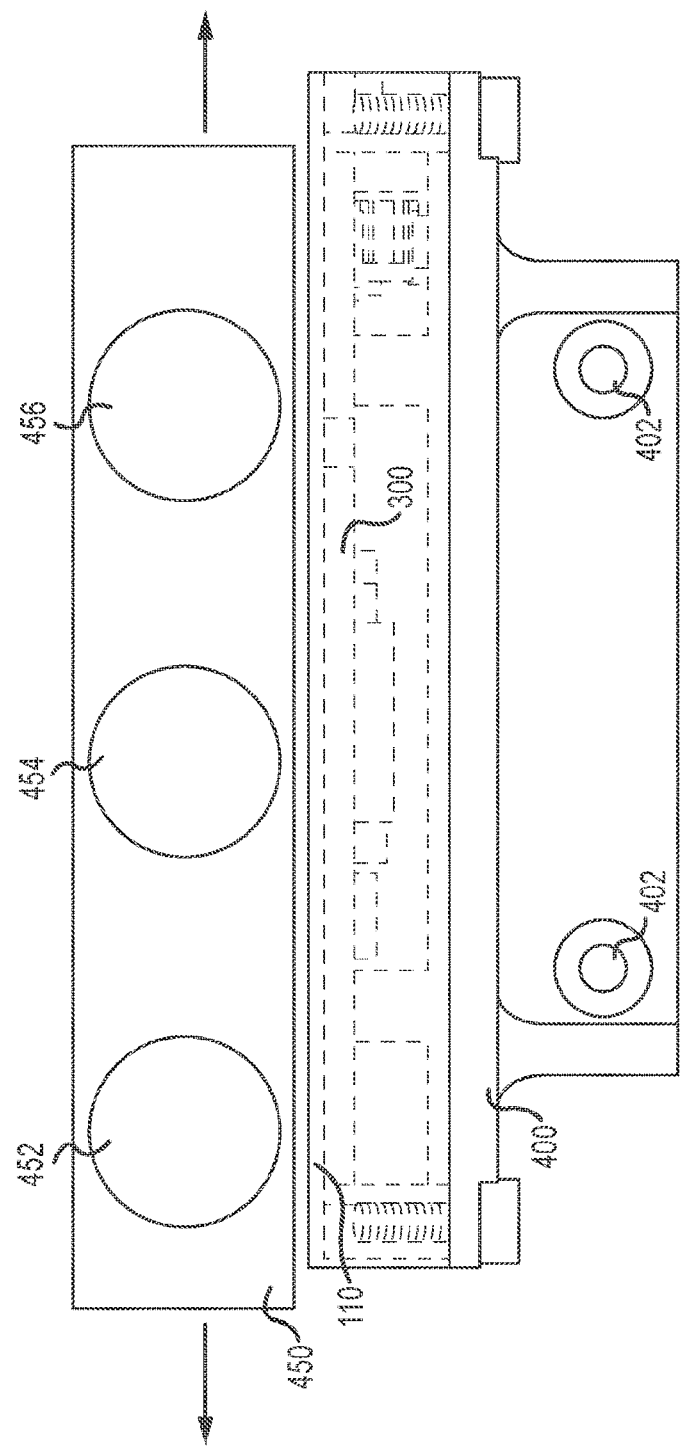
FIG. 7 depicts a perspective view of an embodiment of a sensor mounted relative to a tubing block for selective positioning of a given one of a plurality of tubes relative to the sensor for monitoring the given one of the plurality of tubes.

As described above, a single plate sensor as described herein may be utilized in a variety of contexts in which monitoring a tube 200 for changes between liquid and air in the tube 200 is advantageous. Also described above, a single plate sensor may provide advantages in relation to physical placement of the sensor relative to a tube 200 as the tube 200 need not be particularly placed relative to a plurality of plates, but may be merely placed adjacent to (e.g., within about 2 mm of) the active plate 110. With further reference to FIGS. 6 and 7, an embodiment of a single plate sensor comprising a printed circuit board 300 as described above may be arranged in relation to a mounting chassis 400. The mounting chassis 400 may include mounting holes 402 for engagement of the mounting chassis 400 relative to a device or other support structure. The mounting chassis 400 may include a cover 410, which is shown as being transparent in FIG. 6 for purposes of clarity. In turn, the reference surface 114 may be defined by an exterior portion of the cover 410. The active plate 110 may be disposed below the cover 410 and relative to the reference surface 114 for position relative to a tube 200. The cover 410 may comprise a nonconductive material.

With further reference to FIG. 7, the mounting chassis 400 may be disposed relative to a movable tubing block 450. The tubing block 450 may be operative to engage a plurality of tubes 452-456 (shown in cross section). For instance, as shown in FIG. 7, the tubing block 450 may engage a first tube 452, a second tube 454, and a third tube 456. Additional or fewer tubes may be utilized, and the specific configuration is provided for illustration purposes only.

In any regard, the tubing block 450 may be movable relative to the mounting chassis 400 to dispose different ones of the tubes 452-456 relative to the active plate 110 of the sensor 300. In this regard, relative movement between the tubing block 450 and the mounting chassis 400 may dispose different ones of the plurality of tubes 452-456 relative to the active plate 110 for monitoring of a corresponding given one of the tubes 452-456 that is disposed relative to the active plate 110. For example, the plurality of tubes 452-456 may correspond to tubing associated with different respective fluid sources (e.g., for use and preparing a medication). In this regard, as different source fluids may be used (i.e., as fluid is drawn from a given one of the fluid source), the tubing block 450 may be moved relative to the mounting chassis 400 such that a corresponding respective tube from which the fluid is to be dispensed may be moved in relation to the active plate 110 for monitoring of the tube during use. As the tubing 452-456 need not be placed specifically in relation to a plurality of plates, the relative movement between the tubing block 450 in the mounting chassis 400 may be relatively simple. That is, the tubing 452-456 may need not be placed between opposing plates or in specific relation to a sensor pair. For example, the movement relative between the tubing block 450 and the mounting chassis 400 may be linear (e.g., in the direction of the arrows in FIG. 7) to dispose a respective one of the tubes 452-456 relative to the active plate 110. In this regard, the simplicity of the single plate sensor may allow for relatively simple and efficient placement of a given tube 452-456 relative to the sensor 300 such as, for example, in the context depicted in FIG. 7 whereby a given one of a plurality of tubes may be selectively monitored based on relative placement of the tube in relation to the active sensor 110.

Figure 8:
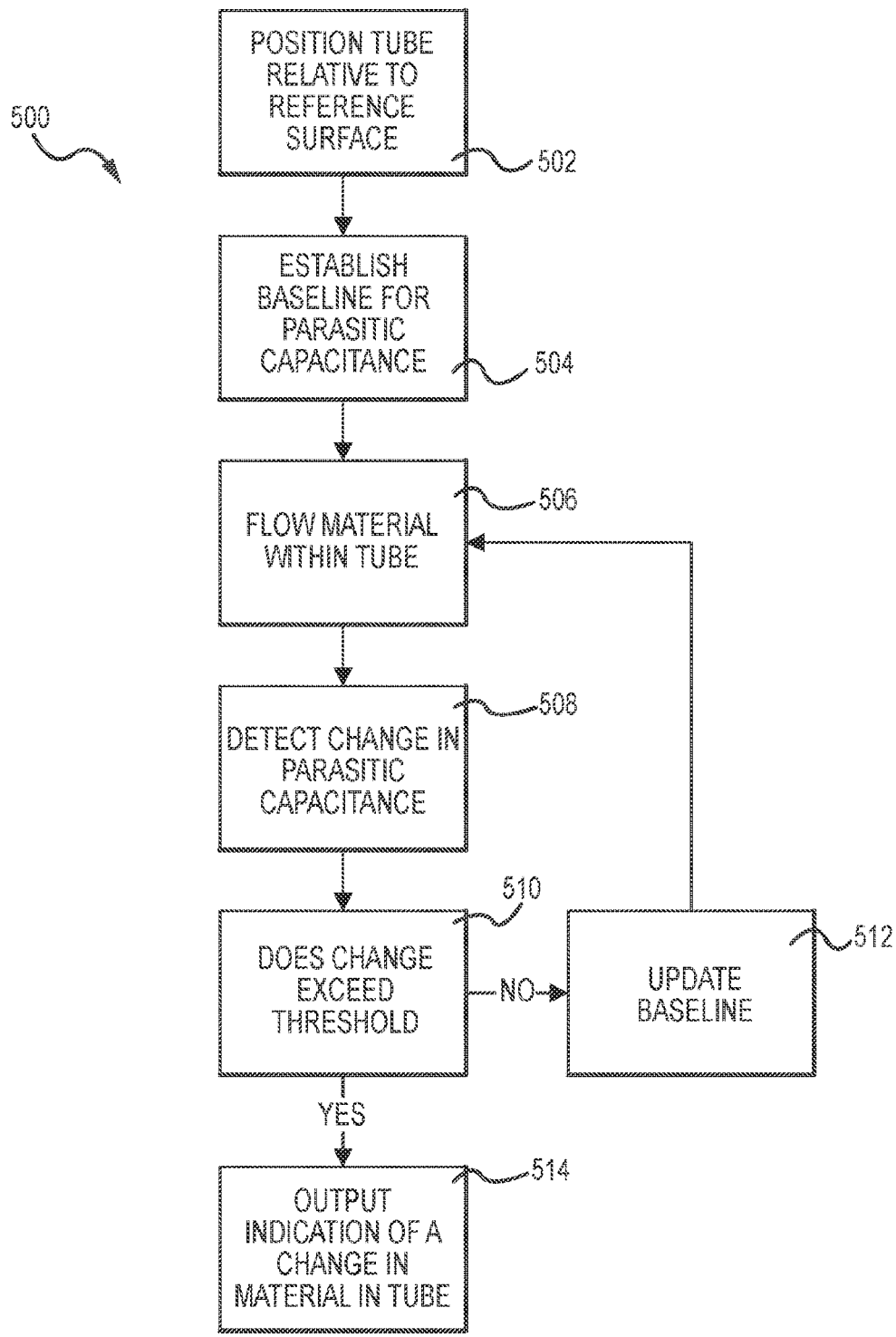
FIG. 8 depicts a flowchart corresponding to an embodiment of a method.

FIG. 8 depicts an embodiment of a method 500 in relation to a single plate capacitive sensor as described above. The method 500 may include positioning 502 a tube in relation to a reference surface. An active plate may be disposed relative to the reference surface adjacent to the tube. The method 500 may include establishing 504 a baseline value for a parasitic capacitance of the active plate. As described above, the establishing 504 may be relative to a known condition in the tube (e.g., the presence of a liquid or a gas). In turn the method 500 may include flowing 506 material within the tube. For instance, the tube may be in fluid communication with a fluid source. As such, the flowing 506 may include controlling flow from the fluid source through the tube 200.

The method 508 may include detecting 508 a change in the parasitic capacitance of the active plate. It may further be determined 510 whether the detected 508 change exceeds a threshold. If the detected 508 change does not occur exceed the threshold, the method 800 may iterate such that the baseline may be updated 512 and the tube is continued to be monitored. For example, the baseline value for the parasitic capacitance may be updated 512 to reflect a relatively slow change in parasitic capacitance that results from changes other than a change in the material in the monitored tube. In turn, the method 500 may continue such that the flowing 506 of material in the tube continues. If it is determined 510 that the detected 508 change exceeds the threshold, the method 500 may include outputting 514 an indication of the detected 508 change between materials in the tube.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for detection of a change between liquid and air in a tube for communicating liquid, comprising:
    establishing a baseline parasitic capacitance value of an active plate of a sensor corresponding to a first known state of an environment surrounding the active plate without reference to any particular ground source, wherein the first known state of the environment comprises one of a liquid filled tube disposed adjacent to the active plate or an air filled tube disposed adjacent to the active plate;
    monitoring a parasitic capacitance value of the active plate relative to the baseline parasitic capacitance value, wherein the parasitic capacitance value is measured without reference to any particular ground source;
    determining the parasitic capacitance value of the active plate exceeds a threshold relative to the baseline parasitic capacitance value; and
    indicating a change in state of the sensor to a second state corresponding to a different state than the first known state, wherein the change in state corresponds to detection of an interface between liquid and air in a tube adjacent to the active plate.

2. The method of claim 1, wherein the threshold comprises a predetermined magnitude of the parasitic capacitance value.

3. The method of claim 2, further comprising:
    updating the baseline parasitic capacitance value of the active plate based on a change in the parasitic capacitance value of the active plate.

4. The method of claim 1, further comprising positioning the liquid filled tube or the air filled tube adjacent to the active plate.

5. The method of claim 1, wherein the active plate comprises a conductive material that is disposed at and extends relative to a reference surface of the sensor, wherein the sensor is devoid of any ground sources in an area coextensive with the extent of the active plate.

6. The method of claim 1, wherein the parasitic capacitance is determined via a measurement module, executed by a processor in operative communication with the active plate.

7. The method of claim 6, wherein the baseline parasitic capacitance value of the active plate is established by a calibration module, executed by a processor.

8. The method of claim 7, wherein the measurement module is operative to detect a change in a material flowing in the tube disposed adjacent to the sensor based on a change in the parasitic capacitance of the active plate relative to the baseline parasitic capacitance.

9. The capacitive sensor of claim 8, wherein the baseline parasitic capacitance is established in relation to the tube containing air, and wherein a change in the parasitic capacitance of the active plate greater than a threshold is indicative of a change to the tube containing a liquid.

10. The capacitive sensor of claim 8, wherein the baseline parasitic capacitance is established in relation to the tube containing liquid, and wherein a change in the parasitic capacitance of the active plate greater than a threshold is indicative of a change to the tube containing air.

11. The capacitive sensor of claim 8, wherein the calibration module is operative to periodically update the baseline parasitic capacitance in response to changes in the parasitic capacitance of the active plate resulting from environmental changes other than a change in material in the tube.

12. The method of claim 1, wherein the sensor includes a printed circuit board and the active plate includes a conductive trace of the printed circuit board.

13. The method of claim 12, wherein a ground plane of the printed circuit board does not overlap any portion of the active plate.

14. The method of claim 1, further comprising a tubing block for engagement of a plurality of tubes, wherein the tubing block is moveable relative to the sensor body to dispose a corresponding one of the plurality of tubes relative to a reference surface such that the corresponding one of the plurality of tubes is disposed adjacent to only the first side of the sensor along the reference surface, and wherein a change in a material flowing in the corresponding one of the plurality of tubes disposed adjacent to the sensor results in the parasitic capacitance of the active plate relative to the environment to change.

15. The method of claim 14, wherein each of the plurality of tubes is engageable with a corresponding different fluid source.

16. The method of claim 15, wherein the corresponding one of the plurality of tubes disposed relative to the reference surface corresponds to a fluid source engaged in a fluid transfer operation.

\* \* \* \* \*